United States Patent
Nonaka et al.

(10) Patent No.: US 12,194,112 B2
(45) Date of Patent: Jan. 14, 2025

(54) INDIUM-CONTAINING TRANSLUCENCY IMPROVING LIQUID FOR DENTAL ZIRCONIA CALCINED BODY

(71) Applicant: SHOFU INC., Kyoto (JP)

(72) Inventors: Kazumichi Nonaka, Kyoto (JP); Shuhei Takahashi, Kyoto (JP)

(73) Assignee: SHOFU INC., Kyoto (JP)

( * ) Notice: Subject to any disclaimer, the term of this patent is extended or adjusted under 35 U.S.C. 154(b) by 101 days.

(21) Appl. No.: 17/502,404

(22) Filed: Oct. 15, 2021

(65) Prior Publication Data

US 2022/0202656 A1 Jun. 30, 2022

(30) Foreign Application Priority Data

Oct. 16, 2020 (JP) .................. 2020-174308

(51) Int. Cl.
*A61K 6/84* (2020.01)
*A61K 6/818* (2020.01)

(52) U.S. Cl.
CPC ............... *A61K 6/84* (2020.01); *A61K 6/818* (2020.01)

(58) Field of Classification Search
CPC ..................................... A61K 6/818
See application file for complete search history.

(56) References Cited

U.S. PATENT DOCUMENTS 9,872,746 B2 * 1/2018 Hauptmann ............ A61C 5/77
2017/0189143 A1 * 7/2017 Wolz ..................... A61K 6/802

FOREIGN PATENT DOCUMENTS

DE 102015103439 9/2016

OTHER PUBLICATIONS

Extended European Search Report issued Apr. 25, 2022 in corresponding European Patent Application No. 21202786.6.
Wolfram W. Rudolph et al., "Indium(III) hydration in aqueous solutions of perchlorate, nitrate and sulfate. Raman and infrared spectroscopic studies and ab-initio molecular orbital calculations of indium(III)-water clusters", Physical Chemistry Chemical Physics, 2004, vol. 6, No. 22, pp. 5145-5155.
Tingjiang Yan et al., "Urea-based hydrothermal growth, optical and photocatalytic properties of single-crystalline In(OH)$_3$ nanocubes", Journal of Colloid and Interface Science, 2008, vol. 325, No. 2, pp. 425-431.

* cited by examiner

*Primary Examiner* — Michael F Pepitone
(74) *Attorney, Agent, or Firm* — Wenderoth, Lind & Ponack, L.L.P.

(57) ABSTRACT

To provide a liquid for improving translucency for dental zirconia calcined body which may impart high translucency which is similar to an enamel of a natural tooth to a zirconia sintered body and a method for using thereof.

The liquid for improving translucency for dental zirconia calcined body of the present disclosure contains a solvent and an indium compound, wherein a content of the indium compound based on the total amount of the liquid improving translucency for dental zirconia calcined body is within a range of 2.0 wt. % to 20.0 wt. % in terms of indium.

13 Claims, No Drawings

INDIUM-CONTAINING TRANSLUCENCY IMPROVING LIQUID FOR DENTAL ZIRCONIA CALCINED BODY

CROSS-REFERENCE TO RELATED APPLICATIONS

This application is based on and claims the benefit of priority from Japanese Patent Application Serial No. 2020-174308 (filed on Oct. 16, 2020), the contents of which are hereby incorporated by reference in their entirety.

BACKGROUND OF THE INVENTION

Field of the Invention

The present disclosure relates to a liquid for improving translucency of a dental zirconia calcined body and a using method thereof.

Description of the Related Art

In recent years, techniques to prepare a prosthesis device by the cutting and machining which uses the dental CAD/CAM system has been spread rapidly and therefore it has been becoming possible to easily prepare prosthetic devices by cutting and machining the mill blanks which are made of ceramic materials such as a zirconia, an alumina and a lithium disilicate glass, or resin materials such as an acrylic resin and a hybrid resin.

In particular, the zirconia has been clinically applied in various cases because of its high strength. On the other hand, the sintered zirconia which can be used in the oral cavity (hereinafter, referred to as "zirconia sintered body") has a very high hardness, and therefore cannot be cut and machined using a dental CAD/CAM system. Thus, a zirconia which is not final but is calcined at a low firing temperature to adjust to a hardness that enables to cut has been used as a zirconia mill blank for dental cutting and machining.

When a zirconia was initially applied as a dental material, the zirconia had high strength but low translucency, and therefore it was mainly used as a coping or a frame. In recent years, because of the development of zirconia with improved translucency (high translucency zirconia), its usages has been expanding from a molar tooth to a full crown of a front tooth. However, even if using high translucency zirconia, the translucency is insufficient to reproduce an enamel of a natural tooth. Therefore, especially in cases where aesthetic property is required, a natural restoration has been prepared by building porcelain on a zirconia. In this situation, it has been desired to prepare a more natural restoration with a full contour zirconia, and therefore, it has been necessary to develop a zirconia having excellent translucency.

Patent Document 1 discloses a liquid for improving translucency containing yttrium and a using method thereof. By using this liquid for a zirconia calcined body, the translucency in an arbitrary part can be improved. However, even if the translucency is improved by this liquid, the translucency is still insufficient for reproducing the color tone of an enamel layer of a natural tooth.

SUMMARY OF THE INVENTION

Technical Problem

A technique for imparting high translucency which is similar to an enamel of a natural tooth to a zirconia sintered body, has been required.

Solution to Problem

The present disclosures made a study on a liquid for improving translucency for dental zirconia calcined body which may impart high translucency which is similar to an enamel of a natural tooth to a zirconia sintered body.

The present disclosure provides a liquid for improving translucency for dental zirconia calcined body, containing, a solvent and an indium compound, wherein a content of the indium compound based on the total amount of the liquid improving translucency for dental zirconia calcined body is within a range of 2.0 wt. % to 20.0 wt. % in terms of indium.

In the liquid for improving translucency for dental zirconia calcined body of the present disclosure, the solvent may be water, alcohol or a mixture thereof.

In the liquid for improving translucency for dental zirconia calcined body of the present disclosure, the liquid for improving translucency for dental zirconia calcined body may further contain a precipitant.

The present disclosure also provides a method for using the liquid for improving translucency for dental zirconia calcined body according to the present disclosure, wherein the liquid for improving translucency for dental zirconia calcined body is applied and/or impregnated to a dental zirconia calcined body.

The present disclosure also provides a method for using the liquid for improving translucency for dental zirconia calcined body according to the present disclosure, wherein the liquid for improving translucency for dental zirconia calcined body is applied to an occlusal plane or an incisal edge side of a dental zirconia calcined body which is cut into a tooth shape.

In this case, the dental zirconia calcined body which is cut into a tooth shape may have a shape of an inlay, a laminate, a crown or a bridge.

Advantageous Effects of Invention

The liquid for improving translucency for dental zirconia calcined body of the present disclosure may impart high translucency which is similar to an enamel of a natural tooth to a zirconia sintered body.

DETAILED DESCRIPTION OF THE PREFERRED EMBODIMENTS

The liquid for improving translucency for dental zirconia calcined body of the present disclosure contains a solvent and an indium compound, wherein a content of the indium compound based on the total amount of the liquid improving translucency for dental zirconia calcined body is within a range of 2.0 wt. % to 20.0 wt. % in terms of indium.

An amount of the indium compound contained in the liquid for improving translucency for dental zirconia calcined body in the present disclosure is more preferably within a range of 5.0 wt. % to 15.0 wt. % in terms of indium. When the amount in terms of indium is less than 2.0 wt. %, sufficient translucency may not be imparted to the zirconia sintered body. On the other hand, when the amount in terms of indium exceeds 20.0 wt. %, sufficient translucency may not be imparted to the zirconia sintered body.

In the present disclosure, the amount of indium in the liquid for improving translucency for dental zirconia calcined body is the most important.

Any known indium compounds which can dissolved in a solvent can be used as an indium compound without any limitation. Specific examples of the indium compound used in the present disclosure include oxides, halides, nitrates, sulfates, organic acid salts of indium, and the like. More specific examples include indium oxide, indium nitrate, indium chloride, indium sulfate, and the like. It is preferable to use indium nitrate since it is easily available and is easy to dissolve in solvents.

Any solvents can be used as the solvent used in the liquid for improving translucency for dental zirconia calcined body in the present disclosure, but specific examples include water, an organic solvent and the like. Water, alcohol and a mixture thereof are particularly preferable since it is easily available and is easy to handle. A specific example of alcohol is ethanol. The solvent is the base material of the liquid for improving translucency for dental zirconia calcined body, and a compounding amount is a remainder of the component compounded in the liquid for improving translucency for dental zirconia calcined body.

The liquid for improving translucency for dental zirconia calcined body in the present disclosure may contain a precipitant for the purpose of inhibiting segregation in a zirconia mill blank for dental cutting and machining. Specific examples of the precipitant include urea, hexamethylene tetramine and the like, but it is preferable to use urea since it is easily available. The concentration of the precipitant is not particularly limited, but is preferably within a range of 5 wt. % to 40 wt. %.

The liquid for improving translucency for dental zirconia calcined body in the present disclosure may contain metal other than indium. Specific examples include yttrium which acts as a stabilizing agent in a zirconia, erbium, iron and cobalt which act as a colorant and the like. Although there is no particular limitation on the concentration of metal other than indium, it is preferable that yttrium is 4 wt. % or less, each metal which acts colorant is 2 wt. % or less, and it is more preferable that the total amount of the metals which act a colorant is 2 wt. % or less. When the concentration of yttrium exceeds 4 wt. %, the translucency tend to be lowered. When the ionic concentration of a metal which acts a colorant exceeds 2 wt. %, it is difficult to reproduce the color tone of a natural tooth.

The liquid for improving translucency for dental zirconia calcined body in the present disclosure may contain a thickener. Specific examples include polyols, glycol ethers and the like. Although there is no particular limitation on the concentration of the thickener, the concentration is preferably 5 wt. % or less, and is more preferably within a range of 0.001 wt. % to 5 wt. %. When the concentration of the thickener exceeds 5 wt. %, it is not preferable because too much time is required for permeation of the liquid for improving translucency.

The liquid for improving translucency for dental zirconia calcined body in the present disclosure may contain a dyeing agent for the purpose of enhancing visibility. It is preferable that the dyeing agent is can be decomposed and removed in the subsequent sintering process. The dyeing agent is preferably an organic dyeing agent, and specific examples include rhodamine, methylene blue and the like. There is no particular limitation on the concentration of the dyeing agent, but the concentration is preferably within a range of 0.01 wt. % to 1 wt. %.

A method for preparing the liquid for improving translucency for dental zirconia calcined body in the present disclosure is not particularly limited, and there is no problem at all with any preparation method as long as a metal compound is dissolved in the solvent.

There is no particular limitation on a method of using the liquid for improving translucency for dental zirconia calcined body in the present disclosure, as long as an arbitrary part of a zirconia calcined body can be permeated and indium can be supported on the part. Specifically, a part or the whole of a zirconia calcined body may be immersed in the liquid for improving translucency for dental zirconia calcined body, or the liquid for improving translucency for dental zirconia calcined body may be applied to a zirconia calcined body with a brush or the like. The specific area for application, for example, can an occlusal plane or an incisal edge side of a dental zirconia calcined body which is cut into a tooth shape.

There is no limitation in a specific atmosphere in which a dental zirconia calcined body is permeated with the liquid for improving translucency for dental zirconia calcined body, and there is no problem in a normal pressure atmosphere, a reduced pressure atmosphere and a pressurized atmosphere. From the viewpoint of shortening the preparation time, a reduced pressure atmosphere or a pressurized atmosphere is preferable as the surrounding environment because of promoting the permeation of the liquid for improving translucency for dental zirconia calcined body. In addition, it is effective for shortening the time of the step in which the liquid for improving translucency for dental zirconia calcined body infiltrates into a space which is in inside of inside of a dental zirconia calcined body and communicates with the outside of the dental zirconia calcined body, that the operation of returning to normal pressure after the pressure reduction operation (pressure reduction/normal pressure operation) or the operation of returning to normal pressure after the pressuring operation (pressuring/normal pressure operation) is repeated multiple times.

The time for immersing a dental zirconia calcined body in the liquid for improving translucency for dental zirconia calcined body is not determined unconditionally and can be adjusted appropriately based on the relative density and the molded body size of the dental zirconia calcined body and the degree of infiltration and the method for immersing of the liquid for improving translucency for dental zirconia calcined body and the like. For example, the time for immersing is usually 1 to 120 hours in the case of immersing, the time for immersing is usually 0.5 to 12 hours in the case of immersing under reduced pressure, and the time for immersing is usually 0.2 to 6 hours in the case of contacting under pressurization.

There is no limitation in the form of a dental zirconia calcined body impregnated with the liquid for improving translucency for dental zirconia calcined body in the present disclosure. The dental zirconia calcined body may have a disk shape or a block shape which is a shape before cutting and machining, or may have a shape of an inlay, a laminate, a crown, a bridge or the like which is a shape after cutting and machining. In addition, it is more preferable embodiment that a dental zirconia calcined body which has a multilayered structure and has a block shape or a disk shape is used for preparing more aesthetic prosthesis device by applying the liquid for improving translucency for dental zirconia calcined body of the present disclosure.

It is preferable that the relative density of a dental zirconia calcined body, which is impregnated with the liquid for improving translucency for dental zirconia calcined body in the present disclosure, is within a range of 50 to 70%. When the relative density is less than 50%, preferable strength and translucency may not be obtained in the sintered body of the dental zirconia calcined body and thus it is not preferable. On the other hand, when the relative density exceeds 70%, the liquid for improving translucency for dental zirconia calcined body may not sufficiently infiltrate. Therefore, in this case, when the zirconia calcined body is sintered, preferable translucency may not be obtained and thus it is not preferable. In the present specifications, the relative density of the zirconia calcined body means an apparent density of the zirconia calcined body which is a semi-sintered body when the density of the perfect sintered body is defined as 100%.

It is preferable that the specific surface area of a dental zirconia calcined body, which is impregnated with the liquid for improving translucency for dental zirconia calcined body in the present disclosure is within a range of 0.5 to 10 m$^2$/g. When the specific surface area is less than 0.5 m$^2$/g, and when the specific surface area exceeds 10 m$^2$/g, preferable translucency may not be obtained in the sintered body of the dental zirconia calcined body and thus it is not preferable.

It is preferable that a dental zirconia calcined body impregnated with the liquid for improving translucency for dental zirconia calcined body in the present disclosure is dried thereafter. Although there is no particular limitation in a drying method, it is preferable to dry in a dryer within a range of 80 to 120 °C. since it can be dried in a short time.

When the liquid for improving translucency for dental zirconia calcined body in the present disclosure is used as a coating liquid, it is preferable that the liquid for improving translucency for dental zirconia calcined body is prepared by mixing all components, and a liquid form which is in a state with the fluidity is preferable. The state of the liquid for improving translucency for dental zirconia calcined body is not limited particularly and specific examples of the state includes a state where all components are uniformly compatible with, a state where the liquid for improving translucency for dental zirconia calcined body is divided into a plurality of layers and a state where a specific component is separated and precipitated. There is no problem particularly as long as the whole is in a uniform state by an operation such as shaking before use. Among them, a liquid form which has fluidity and low viscosity and in which all components are compatible with as described above is preferable from a point of view that liquid for improving translucency for dental zirconia calcined body of the present disclosure infiltrates after applying the liquid for improving translucency for dental zirconia calcined body of the present disclosure to a dental zirconia calcined body.

Furthermore, with respect to an application method to a dental zirconia calcined body by using the liquid for improving translucency for dental zirconia calcined body of the present disclosure, there is no problem in any method as long as the surface of the dental zirconia calcined body is uniformly applied, and any application methods such as application by a brush, spraying using a spray, dropping using a pipette and the like can be used without any problem. Among these, it is preferable to apply using a brush or the like because it can be applied uniformly only to the surface of the dental zirconia calcined body.

When the liquid for improving translucency for dental zirconia calcined body of the present disclosure is used as a coating liquid, it is preferable to apply the liquid for improving translucency for dental zirconia calcined body only to the surface layer of a the dental zirconia calcined body. By doing this, it is possible to improve the transparency of only the surface layer in assuming the tooth crown form, for example, by applying only the enamel part of the tooth crown form, it is possible to maintain the cervical part in the opaque state.

In this way, a zirconia calcined body which is added with indium by the liquid for improving translucency for dental zirconia calcined body in the present disclosure can be prepared.

A method for final firing (sintering) a zirconia calcined body is not particularly limited, but a simple and preferred method is to firing at normal pressure. The firing temperature is not particularly limited, but is preferably within a range of 1450 to 1600 °C., particularly preferably within a range of 1500 to 1600 °C. The holding time at the firing temperature is not particularly limited, but is preferably within a range of 1 minute to 12 hours, and particularly preferably within a range of 2 to 4 hours. The temperature increase rate is not particularly limited, but is preferably within a range of 1 to 400 °C./min, and more preferably within a range of 3 to 100 °C./h.

EXAMPLES

Preparation of Liquid for Improving Translucency

Liquid for improving translucency was prepared by mixing according to the composition shown in Table 1 and then stirring and mixing for 1 hour. Because the weights of an indium source, a nitrate ion and a chloride ion contained in a colorant source and the like are not contained, the total amount of each component in Table 1 is not 100%.

TABLE 1

|  | Solution 1 | Solution 2 | Solution 3 | Solution 4 | Solution 5 | Solution 6 | Solution 7 | Solution 8 |
| --- | --- | --- | --- | --- | --- | --- | --- | --- |
| Indium concentration (wt %) | 3.0 | 6.0 | 10.0 | 15.0 | 20.0 | 10.0 | 10.0 | 10.0 |
| Yttrium concentration (wt %) | 0.0 | 0.0 | 0.0 | 0.0 | 0.0 | 0.0 | 0.0 | 0.0 |
| Solvent (remainder, wt %) | Distilled water (90.7) | Distilled water (81.5) | Distilled water (69.1) | Distilled water (53.6) | Distilled water (38.2) | Distilled water (49.1) | Distilled water (74.5) | Distilled water (68.1) |
| Precipitant (wt %) | — | — | — | — | — | Urea (20.0) | — | — |
| Indium Source | Indium nitrate trihydrate | Indium nitrate trihydrate | Indium nitrate trihydrate | Indium nitrate trihydrate | Indium nitrate trihydrate | Indium nitrate trihydrate | Indium chloride tetrahydrate | Indium nitrate trihydrate |
| Yttrium Source | — | — | — | — | — | — | — | — |
| Thickener (wt %) | — | — | — | — | — | — | — | PVA (1.0) |
| Colorant (wt %) | — | — | — | — | — | — | — | — |
| Colorant Source | — | — | — | — | — | — | — | — |
| Dyeing agent (wt %) | — | — | — | — | — | — | — | — |

TABLE 1-continued

|  | Solution 9 | Solution 10 | Solution 11 | Solution 12 | Solution 13 |
|---|---|---|---|---|---|
| Indium concentration (wt %) | 9.0 | 10.0 | 2.0 | 6.0 | 9.0 |
| Yttrium concentration (wt %) | 0.0 | 0.0 | 1.0 | 0.0 | 0.0 |
| Solvent (remainder, wt %) | Distilled water (69.0) | Distilled water (68.0) | Distilled water (80.7) | Distilled water (95.4) | Distilled water (96.8) |
| Precipitant (wt %) | — | — | — | Urea (40.5) | — |
| Indium Source | Indium nitrate trihydrate | Indium nitrate trihydrate | Indium nitrate trihydrate | Indium nitrate trihydrate | — |
| Yttrium Source | — | — | Yttrium nitrate n-hydrate | — | — |
| Thickener (wt %) | — | — | — | — | — |
| Colorant (wt %) | Fe (0.5) Er (1.0) Co (0.03) | — | — | — | Fe (1.0) Er (1.0) Co (0.03) |
| Colorant Source | Iron nitrate nonahydrate, Erbium nitrate n-hydrate, Cobalt nitrate tetrahydrate | — | — | — | Iron nitrate nonahydrate, Erbium nitrate n-hydrate, Cobalt nitrate tetrahydrate |
| Dyeing agent (wt %) | — | Rhodamine B (0.1) | — | — | — |

|  | Solution 14 | Solution 15 | Solution 16 | Solution 17 | Solution 18 | Solution 19 | Solution 20 | Solution 21 |
|---|---|---|---|---|---|---|---|---|
| Indium concentration (wt %) | 21.0 | 1.5 | 0.0 | 0.0 | 0.0 | 0.0 | 0.0 | 0.0 |
| Yttrium concentration (wt %) | 0.0 | 0.0 | 3.0 | 4.0 | 8.0 | 10.0 | 0.0 | 0.0 |
| Solvent (remainder, wt %) | Distilled water (35.1) | Distilled water (95.4) | Distilled water (86.9) | Distilled water (82.6) | Distilled water (65.2) | Distilled water (56.4) | Distilled water (96.8) | Distilled water (96.8) |
| Precipitant (wt %) | — | — | — | — | — | — | — | — |
| Indium Source | Indium nitrate trihydrate | Indium nitrate trihydrate | — | — | — | — | — | — |
| Yttrium Source | — | — | Yttrium nitrate n-hydrate | Yttrium nitrate n-hydrate | Yttrium nitrate n-hydrate | Yttrium nitrate n-hydrate | — | — |
| Thickener (wt %) | — | — | — | — | — | — | — | — |
| Colorant (wt %) | — | — | — | — | — | — | Fe (0.5) Er (1.0) Co (0.03) | Fe (1.0) Er (1.0) Co (0.03) |
| Colorant Source | — | — | — | — | — | — | Iron nitrate nonahydrate, Erbium nitrate n-hydrate, Cobalt nitrate tetrahydrate | Iron nitrate nonahydrate, Erbium nitrate n-hydrate, Cobalt nitrate tetrahydrate |
| Dyeing agent (wt %) | — | — | — | — | — | — | — | — |

Preparation of zirconia Calcined Body

Zirconia powder containing 5.5 mol % of solid-solved yttria (Zpex SMILE: manufactured by Tosoh Corporation, containing 0.05 wt. % of alumina) was filled in a mold (φ100 mm), and press molding (surface pressure: 50 MPa) was performed to obtain a molded body. Further, the molded body was subjected to CIP treatment (maximum load pressure: 200 MPa, load pressure after releasing: 0 MPa, holding time: 1 minute, repeat times: 10 times). Thereafter, calcination was performed in an electric furnace (1000° C., 30 minutes) to prepare a zirconia calcined body.

Sintering Conditions

The zirconia calcined body was fired in a firing furnace (firing temperature: 1550° C., temperature increase rate: 5° C./min, holding time: 120 minutes) to prepare a zirconia sintered body.

Evaluation of Translucency

The test specimen for evaluating the translucency was prepared by cutting and machining the zirconia calcined body into a round plate shape (φ14 mm×1.6 mm). Each test specimen was sintered in a firing furnace. Then, each test specimen was adjusted to have the thickness (1.0 mm) with a surface grinder. The translucency was evaluated by measuring the contrast ratio. The contrast ratio was measured by using a spectrocolorimeter (manufactured by Konica Minolta). In the following formula, Yw is the value Y measured by placing the white plate behind the test specimen, and Yb is the value Y measured by placing the black plate behind the test specimen. The contrast ratio was calculated from the following formula.

When the contrast ratio value is close to zero, the materials are translucency. When the contrast ratio value is close to 1, the materials are translucency.

Formula: The contrast ratio $= Yb/Yw$

Further, the degree of translucency improvement was calculated from the following formula.

The degree of translucency improvement=(1− (contrast ratio of test specimen)/(contrast ratio of standard product))×100

The standard product was a sintered body that did not use a liquid for improving translucency for dental zirconia calcined body (Comparative Example 8 for Examples 1 to 12, Comparative Example 9 for Example 13, and Comparative Example 7 for Example 14).

The translucency improvement of each test specimen was evaluated by the following ABC score.

A: The degree of translucency improvement 5
B: 5>Translucency improvement≥3
C: 3>Translucency improvement In the case of A, it has a high ability to improve translucency.

In the case of B, it has a certain ability to improve translucency.

In the case of C, it has a low or no ability to improve translucency.

Example 1: The zirconia calcined body was cut and machined into a round plate shape (φ14 mm×1.6 mm) to prepare a test specimen. The prepared test specimen was immersed in solution 1 (room temperature, 1.5 hours). Then, the test specimen was taken out from the solution 1, the solution adhering to the surface was wiped off, and then the test specimen was dried in a dryer (120° C., 1 hour). The test specimen after drying was fired in a firing furnace (firing temperature: 1550° C., temperature increase rate: 5° C./min, holding time: 120 minutes) to prepare a zirconia sintered body.

Example 2: A zirconia sintered body was prepared in the same manner as in Example 1 except that solution 2 was used instead of solution 1.

Example 3: A zirconia sintered body was prepared in the same manner as in Example 1 except that the solution 3 was used instead of the solution 1.

Example 4: A zirconia sintered body was prepared in the same manner as in Example 1 except that solution 4 was used instead of solution 1.

Example 5: A zirconia sintered body was prepared in the same manner as in Example 1 except that the solution 5 was used instead of the solution 1.

Example 6: A zirconia sintered body was prepared in the same manner as in Example 1 except that solution 6 was used instead of solution 1.

Example 7: A zirconia sintered body was prepared in the same manner as in Example 1 except that solution 7 was used instead of solution 1.

Example 8: A zirconia sintered body was prepared in the same manner as in Example 1 except that solution 8 was used instead of solution 1.

Example 9: A zirconia sintered body was prepared in the same manner as in Example 1 except that solution 9 was used instead of the solution 1.

Example 10: A zirconia sintered body was prepared in the same manner as in Example 1 except that the solution 10 was used instead of the solution 1.

Example 11: A zirconia sintered body was prepared in the same manner as in Example 1 except that the solution 11 was used instead of the solution 1.

Example 12: A zirconia sintered body was prepared in the same manner as in Example 1 except that the solution 12 was used instead of the solution 1.

Example 13: A zirconia sintered body was prepared in the same manner as in Example 1 except that the solution 13 was used instead of the solution 1.

Example 14: A test specimen having a single crown shape of a left maxillary central incisor was prepared by cutting and machining from a zirconia calcined body. Solution 3 was applied to the prepared test specimen five times with a brush. In the first application, the solution was applied in the range of about ½ of the total length from an incisal edge portion. In the second application, the solution was applied in the range of about ⅓ of the total length from the incisal edge portion. In the third application, the solution was applied in the range of about ¼ of the total length from the incisal edge portion. In the fourth and the fifth application, the solution applied in the range of ⅕ of the total length from the incisal edge portion. Then, after drying in a dryer (120° C., 1 hour), a restoration having the single crown shape of a left maxillary central incisor was prepared by firing in a firing furnace (firing temperature: 1550° C., temperature increase rate: 5° C./min, holding time: 120 minutes).

Comparative Example 1: A zirconia sintered body was prepared in the same manner as in Example 1 except that solution 14 was used instead of solution 1.

Comparative Example 2: A zirconia sintered body was prepared in the same manner as in Example 1 except that solution 15 was used instead of solution 1.

Comparative Example 3: A zirconia sintered body was prepared in the same manner as in Example 1 except that solution 16 was used instead of solution 1.

Comparative Example 4: A zirconia sintered body was prepared in the same manner as in Example 1 except that solution 17 was used instead of solution 1.

Comparative Example 5: A zirconia sintered body was prepared in the same manner as in Example 1 except that solution 18 was used instead of solution 1.

Comparative Example 6: A zirconia sintered body was prepared in the same manner as in Example 1 except that solution 19 was used instead of solution 1.

Comparative Example 7: A zirconia sintered body was prepared in the same manner as in Example 1 except that solution 20 was used instead of solution 1.

Comparative Example 8: A zirconia sintered body was prepared in the same manner as in Example 1 except that immersion in the solution was not performed.

Comparative Example 9: A zirconia sintered body was prepared in the same manner as in Example 13 except that solution 21 was used instead of solution 13.

Comparative Example 10: A restoration of maxillary left central incisor with a single crown shape was prepared in the same manner as in Example 14 except that no solution was applied.

Table 2 shows the characteristic test results of the prepared zirconia mill blank for dental cutting and machining in Examples and Comparative Examples.

TABLE 2

|  | Example 1 | Example 2 | Example 3 | Example 4 | Example 5 | Example 6 | Example 7 | Example 8 | Example 9 | Example 10 | Example 11 | Example 12 | Example 13 |
|---|---|---|---|---|---|---|---|---|---|---|---|---|---|
| Liquid for improving translucency | Solution 1 | Solution 2 | Solution 3 | Solution 4 | Solution 5 | Solution 6 | Solution 7 | Solution 8 | Solution 9 | Solution 10 | Solution 11 | Solution 12 | Solution 13 |
| Contrast ratio | 0.66 | 0.64 | 0.62 | 0.65 | 0.66 | 0.62 | 0.62 | 0.62 | 0.72 | 0.62 | 0.66 | 0.64 | 0.80 |
| Degree of translucency improvement | 4.35 | 7.25 | 10.1 | 5.80 | 4.35 | 10.1 | 10.1 | 10.1 | 12.20 | 10.14 | 4.35 | 7.25 | 10.11 |
| Evaluation | B | A | A | A | B | A | A | A | A | A | B | A | A |

TABLE 2-continued

|  | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| Liquid for improving translucency | Solution 14 | Solution 15 | Solution 16 | Solution 17 | Solution 18 | Solution 19 | Solution 20 | — | Solution 21 |
| Contrast ratio | 0.67 | 0.67 | 0.67 | 0.67 | 0.69 | 0.72 | 0.82 | 0.69 | 0.89 |
| Degree of translucency improvement | 2.90 | 2.90 | 2.90 | 2.90 | 0.00 | −4.35 | — | — | — |
| Evaluation | C | C | C | C | C | C | — | — | — |

In Examples 1 to 13, since the solution in which an indium concentration was within a range of 2.0 to 20.0 wt. % was used, the translucency was sufficiently improved and a translucency similar to a natural tooth was exhibited.

In Comparative Examples 1 to 7 and 9, since the solution in which an indium concentration was less than 2.0 wt. % or more than 20.0 wt. % was used, the translucency was not sufficiently improved and a translucency similar to a natural tooth was not exhibited.

The prosthesis of Example 14 gradually improved in translucency from the middle part of the prosthesis toward the incision, and had an appearance similar to a natural tooth.

In the prosthesis of Comparative Example 10, the entire prosthesis had the same insufficient translucency, and had an appearance different from a natural tooth.

With respect to the use of substantially any plural and/or singular terms herein, those having skill in the art can translate from the plural to the singular and/or from the singular to the plural as is appropriate to the context.

Although the description herein has been given with reference to the embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The present disclosure relates to a liquid for improving a translucency of a zirconia dental article and a using method thereof, and is a technique which can be used in the dental field.

What is claimed is:

1. A liquid for improving translucency for dental zirconia calcined body, containing,
    a solvent, a precipitant, and an indium compound, wherein
    a content of the indium compound based on the total amount of the liquid for improving translucency for dental zirconia calcined body is within a range of 2.0 wt. % to 20.0 wt. % in terms of indium.

2. The liquid for improving translucency for dental zirconia calcined body according to claim 1, wherein
    the solvent is water, alcohol or a mixture thereof.

3. A method for using the liquid for improving translucency for dental zirconia calcined body according to claim 1, comprising
    applying and/or impregnating the liquid for improving translucency for dental zirconia calcined body to a dental zirconia calcined body.

4. A method for using the liquid for improving translucency for dental zirconia calcined body according to claim 1, comprising
    applying the liquid for improving translucency for dental zirconia calcined body to an occlusal plane or an incisal edge side of a dental zirconia calcined body which is cut into a tooth shape.

5. The method for using the liquid for improving translucency for dental zirconia calcined body according to claim 4, wherein
    the dental zirconia calcined body which is cut into a tooth shape has a shape of an inlay, a laminate, a crown or a bridge.

6. The liquid for improving translucency for dental zirconia calcined body according to claim 1, wherein
    the content of the indium compound based on the total amount of the liquid for improving translucency for dental zirconia calcined body is within a range of 5.0 wt. % to 15.0 wt. % in terms of indium.

7. The liquid for improving translucency for dental zirconia calcined body according to claim 1, wherein
    a concentration of the precipitant is within a range of 5 wt. % to 40 wt. %, and
    the content of the indium compound based on the total amount of the liquid for improving translucency for dental zirconia calcined body is within a range of 5.0 wt. % to 15.0 wt. % in terms of indium.

8. The liquid for improving translucency for dental zirconia calcined body according to claim 1, wherein
    the precipitant comprises urea.

9. The liquid for improving translucency for dental zirconia calcined body according to claim 1, wherein
    the liquid for improving translucency for dental zirconia calcined body further contains yttrium, and a concentration of the yttrium is 4 wt. % or less.

10. The liquid for improving translucency for dental zirconia calcined body according to claim 1, wherein
    the liquid for improving translucency for dental zirconia calcined body further contains a thickener, and a concentration of the thickener is 5 wt. % or less.

11. The liquid for improving translucency for dental zirconia calcined body according to claim 1, wherein
    the liquid for improving translucency for dental zirconia calcined body further contains a dyeing agent, and a concentration of the dyeing agent is within a range of 0.01 wt. % to 1 wt. %.

12. The method for using the liquid for improving translucency for dental zirconia calcined body according to claim 4, wherein
    a relative density of the dental zirconia calcined body is within a range of 50 to 70%.

13. The method for using the liquid for improving translucency for dental zirconia calcined body according to claim 4, wherein
a specific surface area of the dental zirconia calcined body is within a range of 0.5 to 10 m²/g.

* * * * *